(12) United States Patent  
Luce (10) Patent No.: US 6,726,625 B2  
(45) Date of Patent: Apr. 27, 2004

(54) NON-CONTACT TONOMETER HAVING IMPROVED AIR PUMP

(75) Inventor: David A. Luce, Clarence Center, NY (US)

(73) Assignee: Reichert, Inc., Depew, NY (US)

( * ) Notice: Subject to any disclaimer, the term of this patent is extended or adjusted under 35 U.S.C. 154(b) by 193 days.

(21) Appl. No.: 10/117,510

(22) Filed: Apr. 5, 2002

(65) Prior Publication Data

US 2003/0191381 A1 Oct. 9, 2003

(51) Int. Cl.[7] .................................................. A61B 3/16
(52) U.S. Cl. .................................................... 600/401
(58) Field of Search ................................. 600/398, 401, 600/405

(56) References Cited

U.S. PATENT DOCUMENTS 3,585,849 A      6/1971  Grolman
4,947,849 A  *  8/1990  Takahashi et al. .......... 600/401
4,996,990 A  *  3/1991  Hideshima ................... 600/401
5,048,526 A  *  9/1991  Tomoda ....................... 600/401
5,301,598 A  *  4/1994  Sonnabend .................... 92/84
5,957,381 A  *  9/1999  Wakamatsu et al. .......... 239/88

* cited by examiner

Primary Examiner—Eric F. Winakur
(74) Attorney, Agent, or Firm—Hodgson Russ LLP (57) ABSTRACT

A non-contact tonometer of a type having a cylinder, a piston received by the cylinder for axially directed movement relative to the cylinder, and a driven member for causing the piston to move relative to the cylinder in a compression stroke to generate a fluid pulse for transfiguring a cornea is improved by decoupling the piston from the driven member to eliminate the need for critical alignment between the driven member and piston and allow the piston to be self-aligning with respect to the cylinder.

29 Claims, 6 Drawing Sheets

NON-CONTACT TONOMETER HAVING IMPROVED AIR PUMP

FIELD OF THE INVENTION

The present invention relates generally to ophthalmic instruments, and more particularly to non-contact tonometers that measure intraocular pressure (IOP) by directing a fluid pulse at an eye to transfigure the cornea.

BACKGROUND OF THE INVENTION

Non-contact tonometers are well-known in the field of ophthalmology for measuring intraocular pressure (IOP) by directing a fluid pulse at the cornea to cause observable deformation of the cornea. Most commonly, the observable deformation is a flattening of a predetermined area of the cornea, a condition known as applanation. In prior art non-contact tonometers, the fluid pulse is generated by a fluid pump system defining a plenum chamber for pressurized fluid. In order to direct the fluid pulse at the patient's cornea, a narrow cylindrical fluid discharge tube is arranged in flow communication with the plenum chamber.

A common fluid pump system found in non-contact tonometers includes a rotary solenoid having a driven armature, a piston rod pivotally coupled to the solenoid armature, a piston fixed to the end of the piston rod for travel therewith, and a cylinder receiving the piston in close slidable fit to allow axial movement of the piston relative to the cylinder during a compression stroke. An example of this type of fluid pump system can be seen in U.S. Pat. No. 3,585,849 issued Jun. 22, 1971. In fluid pump systems of the type described, the driven armature, piston rod, and piston are connected in series, and thus the radial position of the piston in the cylinder is influenced by the driven armature and piston rod. Consequently, the solenoid, piston rod, piston and cylinder must be manufactured and located according to close tolerances to ensure that the piston moves in axial alignment with the cylinder during a compression stroke.

In more recent non-contact tonometers, linear motors are used to drive the piston. The piston is either directly coupled to an axially driven armature of the linear motor, or is indirectly coupled to the axially driven armature by a piston rod to which the piston is fixed. Here again, the components of the fluid pump system must be manufactured and mounted in the instrument according to close tolerances to ensure axial alignment of the piston with the cylinder for providing reliable and repeatable performance.

The necessity to design, manufacture, and assemble component parts of the fluid pump system of a non-contact tonometer pursuant to critical tolerance specifications adds to the production time and cost of the instrument. Despite time consuming and expensive efforts to provide a smooth and repeatable piston compression stroke, fluid pump systems of the prior art are accompanied by performance limitations caused by the interconnection of the various system components.

SUMMARY OF THE INVENTION

Therefore, it is an object of the present invention to provide a non-contact tonometer with an improved fluid pump system that is easier, less costly, and faster to design and manufacture.

It is another object of the present invention to provide a non-contact tonometer with a fluid pump system that exhibits improved performance over tonometer fluid pump systems of the prior art.

It is a further object of the present invention to provide a non-contact tonometer with an improved fluid pump system that involves relaxed tolerances in manufacture and assembly alignment, and which avoids the need for complex universal joint couplings.

The invention is embodied in a non-contact tonometer of a general type comprising a fluid pump system, a fluid discharge tube in communication with the fluid pump system for directing a fluid pulse at a patient's eye to cause applanation of the cornea, applanation detection means for monitoring the cornea to detect applanation caused by the fluid pulse, means for determining a fluid pressure within a plenum chamber of the fluid pump system at a moment when the cornea reaches applanation, and processing means for correlating the plenum pressure with an intraocular pressure of the patient's eye. In accordance with a preferred embodiment of the present invention, the fluid pump system comprises a linear solenoid having a driven member in the form of a plunger that moves axially when the solenoid is energized, and a piston situated adjacent an abutment end of the plunger for engagement thereby. The piston is not coupled to the plunger, but is merely pushed during a compression stroke to move axially relative to a surrounding cylinder with which the piston cooperates to define a compression chamber. A spring bearing against a front wall of the cylinder and a leading surface of the piston provides return motion to the piston. As will be appreciated, decoupling the piston from the solenoid plunger makes the axial alignment of the piston relative to the cylinder independent of the axial alignment of the plunger relative to the cylinder. In other words, the piston will remain aligned for slidable axial movement within the cylinder even if the plunger is "off center" with respect to the cylinder and/or piston. Thus, the present invention allows for relaxation of tolerances and ensures that the piston remains in axial alignment with the cylinder over time for generating a more consistent air pulse to improve measurement performance.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
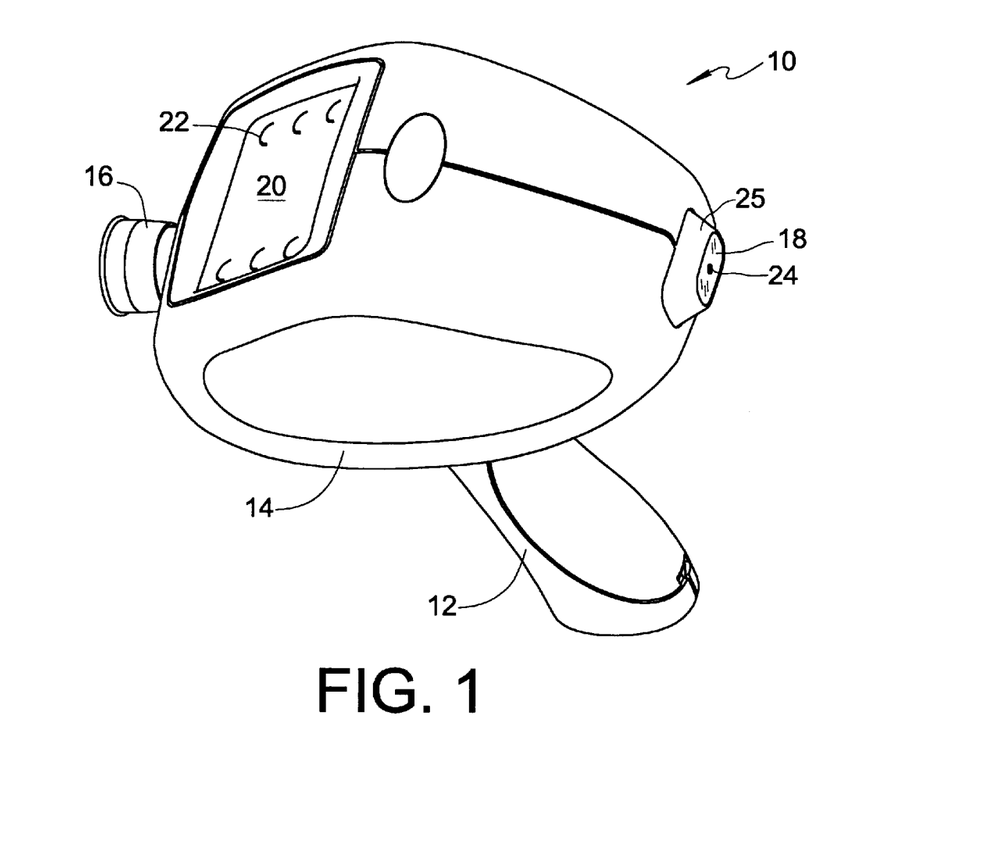
FIG. 1 is a perspective view of a non-contact tonometer formed in accordance with a preferred embodiment of the present invention.

FIG. 1 of the drawings shows a non-contact tonometer (NCT) 10 embodying the present invention. NCT 10 is depicted as being a handheld instrument having a handle portion 12 and a head portion 14 at the top of the handle portion. While the present invention is described in the context of a handheld NCT, it can also be embodied in a table-top NCT. Handle portion 12 houses a rechargeable power source for energizing alignment and tonometric measurement systems carried by head portion 14. Also visible in FIG. 1 is an operator eyepiece 16 at one end of head portion 14, a front window 18 at an opposite end of head portion 14 for facing a patient, and a liquid crystal display 20 with pushbutton control overlay 22 angled toward the operator near operator eyepiece 16.

Figure 2:
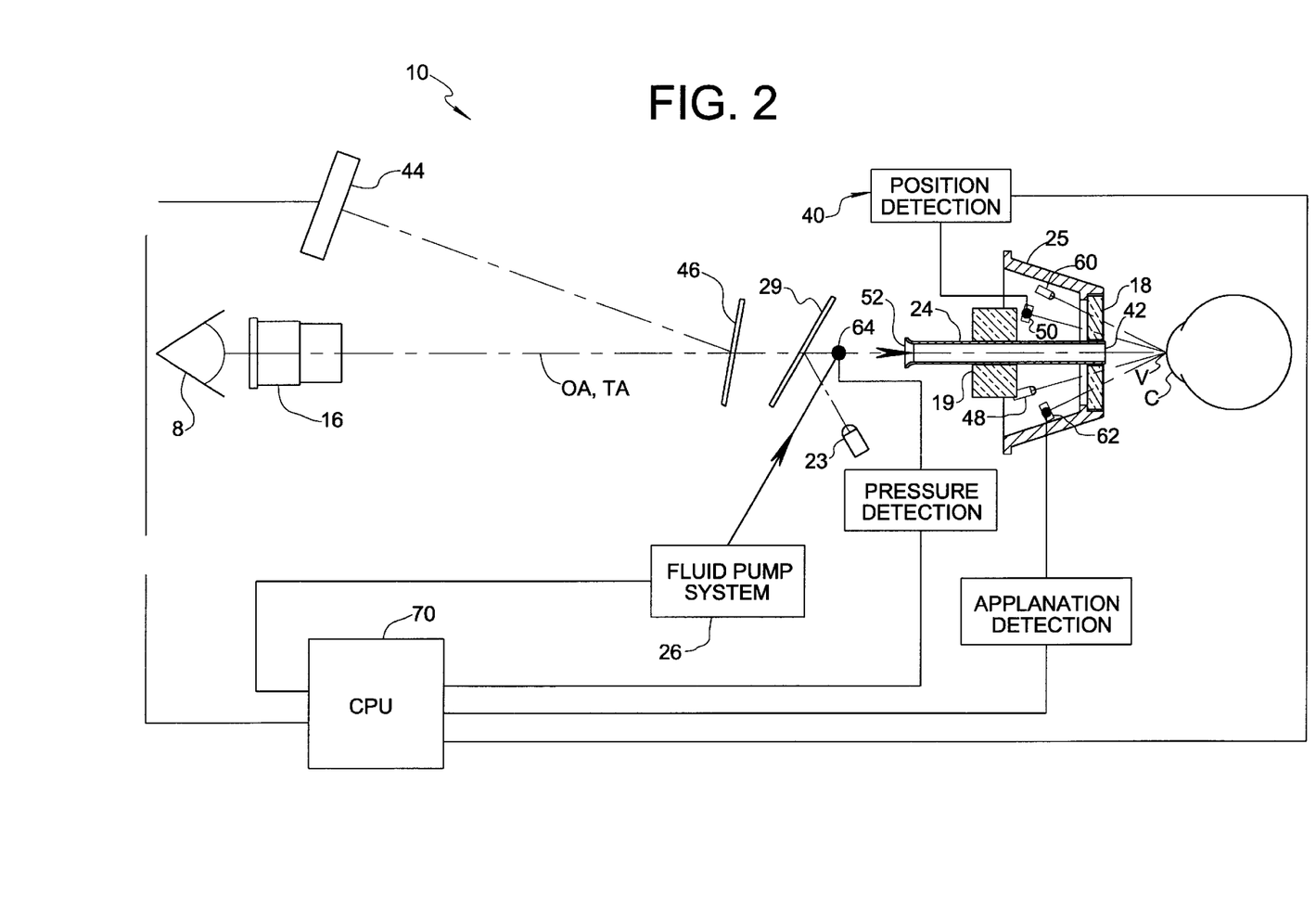
FIG. 2 is a schematic diagram of the non-contact tonometer shown in FIG. 1.

FIG. 2 provides a schematic representation of the alignment and tonometric measurement systems housed by head portion 14. NCT 10 is operable to discharge a fluid pulse through a fluid discharge tube 24 aligned along a test axis TA to cause observable deformation of a patient's cornea C for purposes of measuring intraocular pressure. The fluid pulse is generated by a fluid pump system 26 communicating with fluid discharge tube 24, which extends through a nosepiece 25 fixed to a mounting member 27 seen in FIG. 3.

As a prerequisite to testing, it is necessary for an operator 8 to align NCT 10 in three dimensions (X-Y-Z alignment) relative to the patient's eye. The patient is instructed to gaze at a target image presented along optical axis OA by a target light source 23 and a beam splitter 29. The operator 8 is preferably guided in coarse alignment of NCT 10 by viewing the patient's eye through operator eyepiece 16 along an optical axis OA that coincides with test axis TA. A planar— planar objective lens 19 on optical axis OA cooperates with front window 18 to support fluid discharge tube 24 without blocking the operator's view of the patient's eye. In a preferred embodiment, an opto-electronic position detection system 40 associated with nosepiece 25 senses the position of an outlet orifice 42 of fluid discharge tube 24 relative to a corneal vertex V and provides signal information used to drive an instructive "heads up" display 44 providing real time X, Y, and Z alignment cues. An image of instructive display 44 is projected to the operator along optical axis OA by a beam splitter 46, such that the instructive display image is optically superimposed with an image of the patient's eye as viewed by the operator. Proper alignment is confirmed by position detection system 40. Reference numerals 48 and 50 respectively denote an emitter and a detector of position detection system 40. Commonly owned U.S. patent application Ser. No. 09/992,875, filed Nov. 6, 2001 and incorporated herein by reference in its entirety, describes a preferred alignment system in greater detail at paragraphs [0022] through [0036] and FIGS. 3–10.

Alternative means for aligning NCT 10 are also possible. By way of non-limiting example, NCT 10 may include an alignment system as taught in U.S. Pat. No. 4,881,807, wherein the operator views a video display of the eye with superimposed instructional graphics. If NCT 10 is designed as an inexpensive screening tool wherein measurement accuracy requirements can be relaxed to reduce cost, it is conceivable to have a "go/no go" alignment system that simply confirms proper alignment without providing any instructional display or graphics to the operator. An example of a "go/no go" alignment system is described in commonly owned U.S. Pat. No. 6,361,495.

Figure 3:
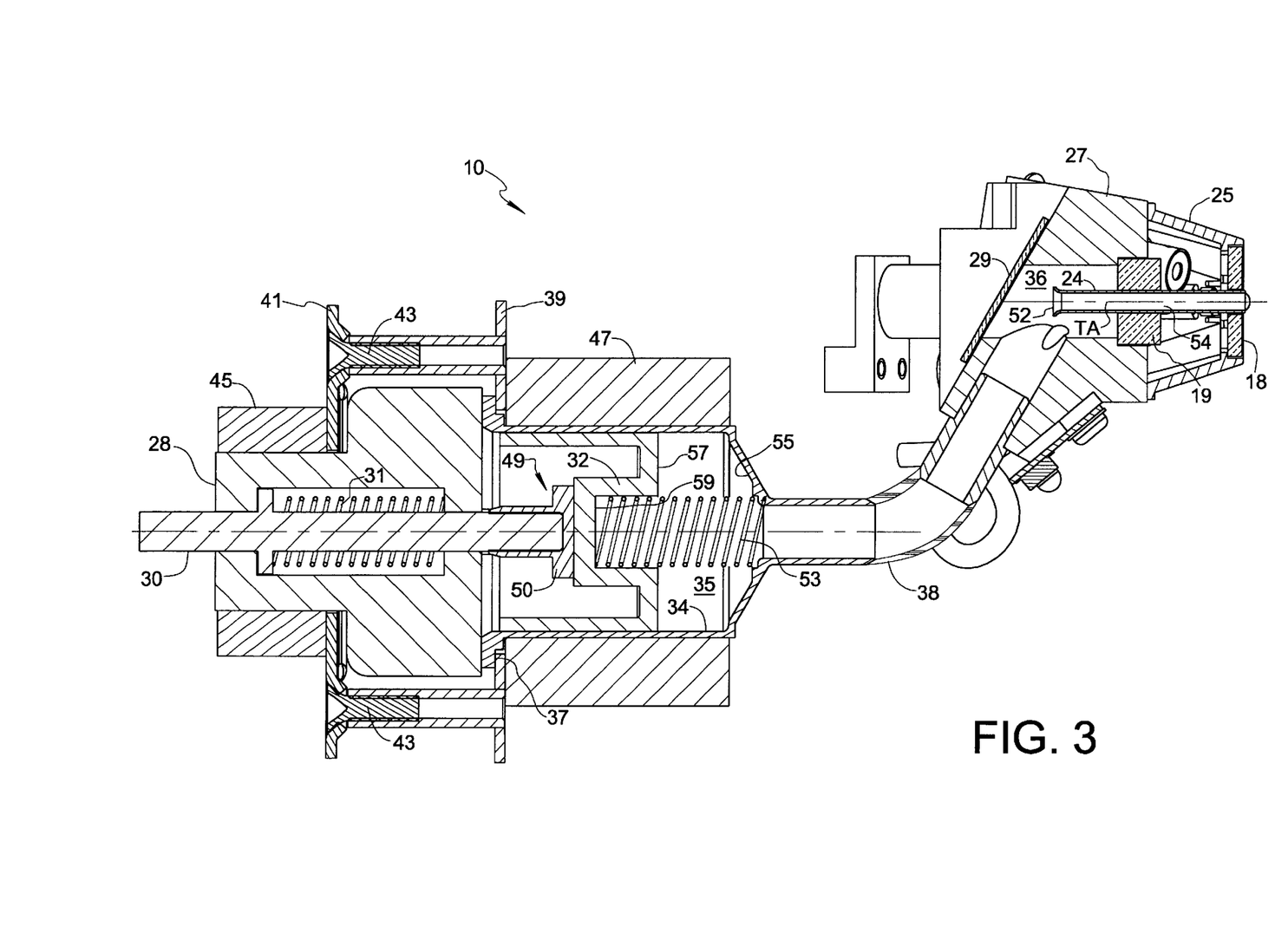
FIG. 3 is a cross-sectional view of a nosepiece and associated fluid pump system of the non-contact tonometer shown in FIG. 1.
Figure 4:
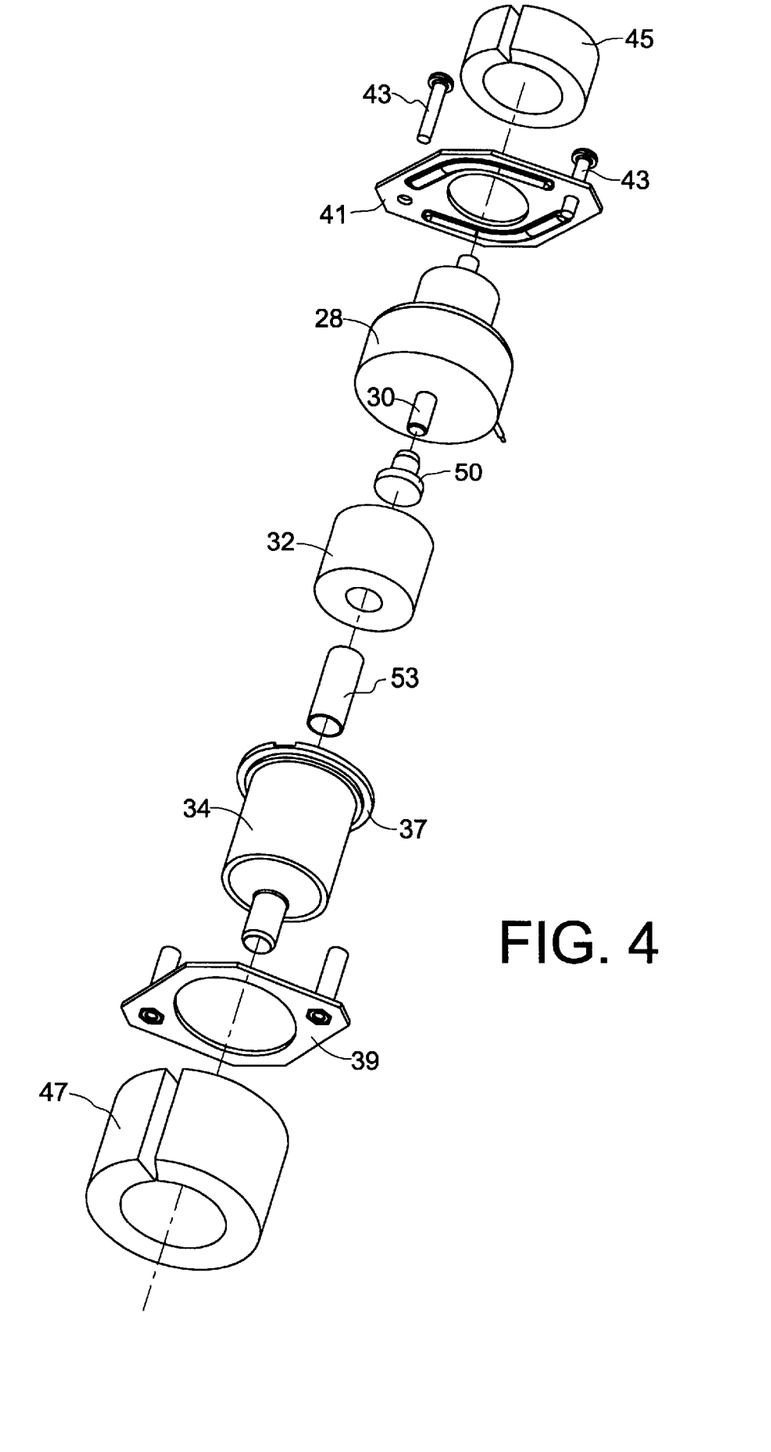
FIG. 4 is an exploded perspective view of the fluid pump shown in FIG. 3.

Once proper alignment of NCT 10 is achieved, fluid pump system 26 is triggered to generate a fluid pulse. Referring to FIGS. 3 and 4, fluid pump system 26 preferably comprises a linear solenoid 28 having a plunger 30, a piston 32 driven by plunger 30 and slidably received by a corresponding cylinder 34 to compress air within a compression chamber 35 when solenoid 28 is energized, and a plenum chamber 36 in flow communication with compression chamber 35 by way of a fluid conduit 38. Fluid discharge tube 24 extends into and communicates with plenum chamber 36, thus enabling flow communication between compression chamber 35 and discharge tube 24.

In accordance with the present invention, piston 32 is unattached to plunger 30 and is merely pushed by the plunger during a compression stroke. As a result, the axial alignment of piston 32 with cylinder 34 is in no way dependent upon the axial alignment of plunger 30 with cylinder 34. As will be appreciated, this decoupled arrangement of plunger 30 and piston 32 removes the need for critical alignment between the plunger and piston, and makes it simpler to assemble components of fluid pump system 26. In the embodiment depicted in FIGS. 3 and 4, cylinder 34 includes a flange 37 enabling the cylinder to simply be clamped to linear solenoid 28 by a solenoid plate assembly 39 and a solenoid plate 41 adjustable relative to the solenoid plate assembly by operation of threaded fasteners 43. A solenoid wrap 45 and a cylinder wrap 47 of synthetic rubber, foam or other damping material are also shown in FIGS. 3 and 4. Because piston 32 is independent from plunger 30, the piston is unrestricted by the plunger with respect to its radial degree of freedom and therefore is self-aligning relative to corresponding cylinder 34. As a result, the fluid pump system provides a more consistent fluid pulse over time because slight alignment shifts in the mounting and position of the solenoid after a large number of cycles do not affect the axial alignment of the piston relative to the cylinder.

Plunger 30 is characterized by an abutment end 49 that preferably includes a protective cap 50 of plastic or other suitable material to maintain substantially wear-free engagement between the plunger and piston 32.

Solenoid 28 preferably includes a means for returning plunger 30 to an initial reference position as illustrated in FIG. 3. Commonly, the return means is a spring 31 acting on the plunger. Because piston 32 is not attached to plunger 30, a spring 53 is provided to act between cylinder 34 and piston 32 to return the piston to its stroke start position illustrated in FIG. 3. In a preferred assembly, spring 53 is a coil spring that bears against a front wall 55 of cylinder 34 and a leading surface 57 of piston 32, and is arranged to be coaxial with the piston and cylinder. A recess 59 provided in piston leading surface 57 receives an end of spring 53 to help locate and hold the spring in place.

Figure 5:
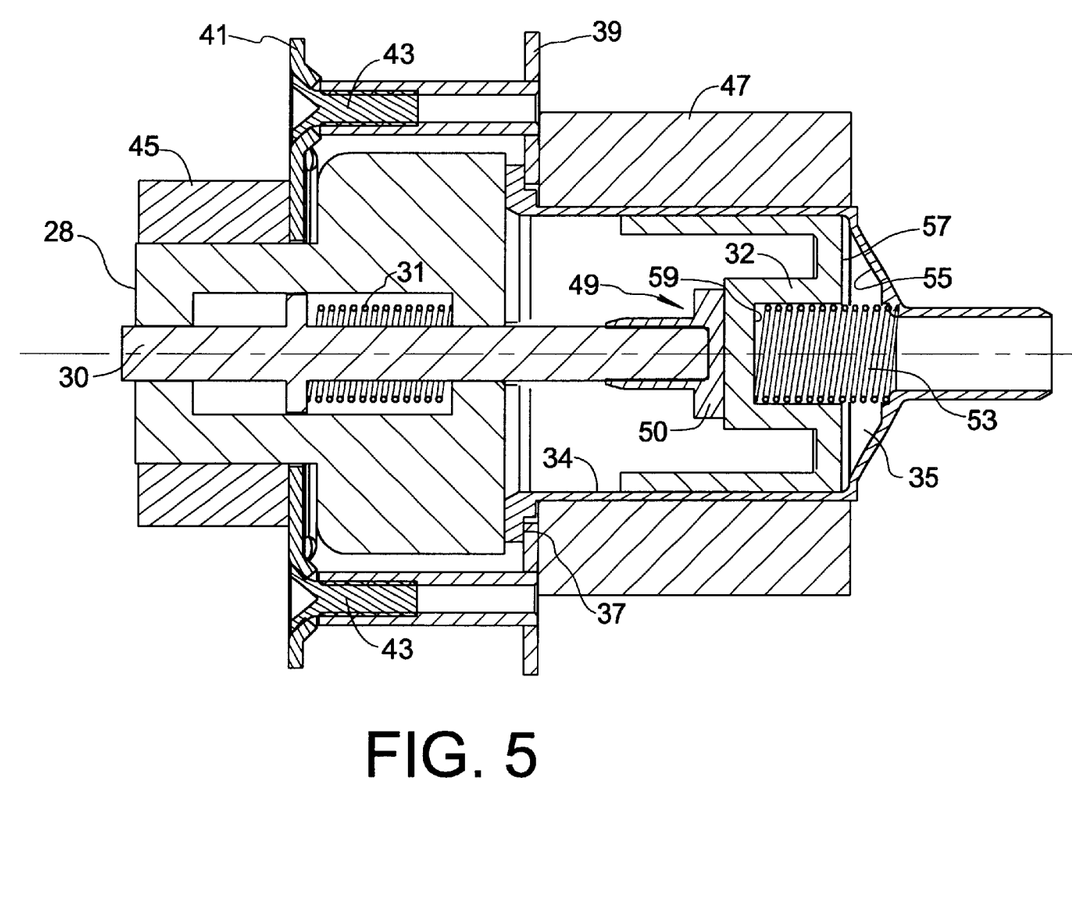
FIG. 5 is a cross-sectional view showing a compression stroke of the fluid pump shown in FIG. 3.

FIG. 5 shows fluid pump system 26 during a compression stroke. When solenoid 28 is energized, plunger 30 is forced from its initial reference position to the left in FIG. 5, pushing piston 32 from its stroke start position into cylinder 34 to compress fluid within compression chamber 35. This action loads solenoid spring 31 and piston spring 53 in compression so that when solenoid 28 is de-energized, solenoid spring 31 forces plunger 30 to return to its initial reference position and piston spring 53 forces piston 32 back to its stroke start position. Piston spring 53 may be selected with a suitable spring constant for returning piston 32 to its stroke start position in a relatively slow manner to reduce back flow of external air into the discharge tube. By contrast, in prior art non-contact tonometers wherein the piston and driven member are coupled together, return of the piston is governed by the solenoid return spring and cannot be independently controlled. Typically, solenoid return springs, in commercially available solenoids are chosen to provide a very rapid return of the driven member to its initial reference position, contributing to back flow. Therefore, it may be desirable to choose piston spring 53 such that piston 32 is returned to its stroke start position more slowly than plunger 30 is returned to its initial reference position by solenoid spring 31.

Figure 6:
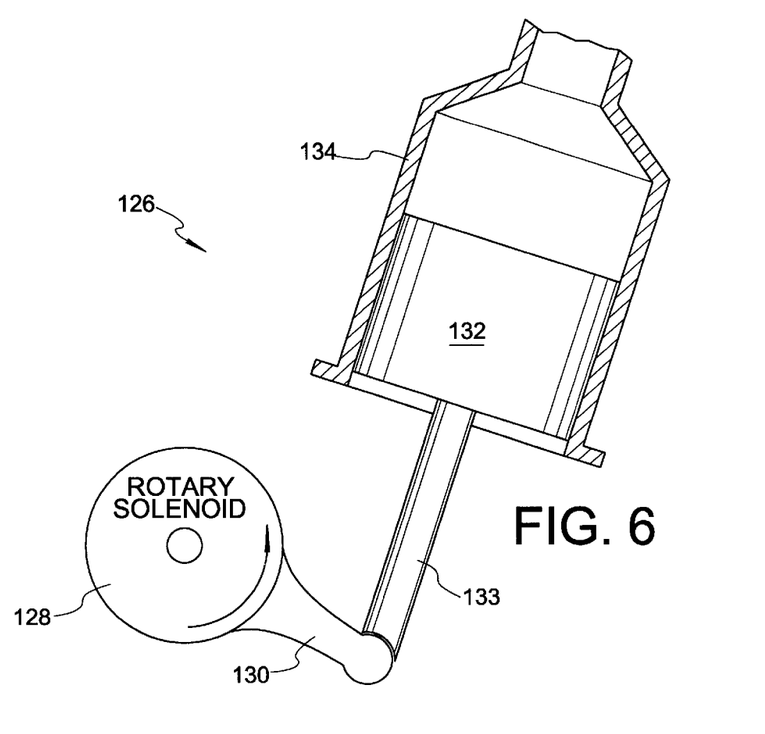
FIG. 6 is a cross-sectional view of a fluid pump formed in accordance with an alternative embodiment of the present invention.

As will be understood from FIG. 6, the principle of the present invention can be applied to a tonometer fluid pump system 126 employing a rotary solenoid 128 that pivots an armature 130 counterclockwise as seen in FIG. 6 in response to energizing current. In the embodiment of FIG. 6, armature 130 is a driven member that pushes against but is unattached to a piston rod 133. The abutting surfaces of armature 130 and piston rod 133 may be complementary curved surfaces to accommodate the translation of rotary motion to linear motion. A piston 132 fixed to piston rod 133 is therefore independent from driven armature 130 with respect to its alignment relative to a corresponding cylinder 134. This embodiment further illustrates that the driven member (i.e. armature 130) need not be directly in contact with the piston, but can be arranged in contact with an intermediate member such as piston rod 133, and that decoupling can be introduced at any point between the driven member and piston.

Figure 7:
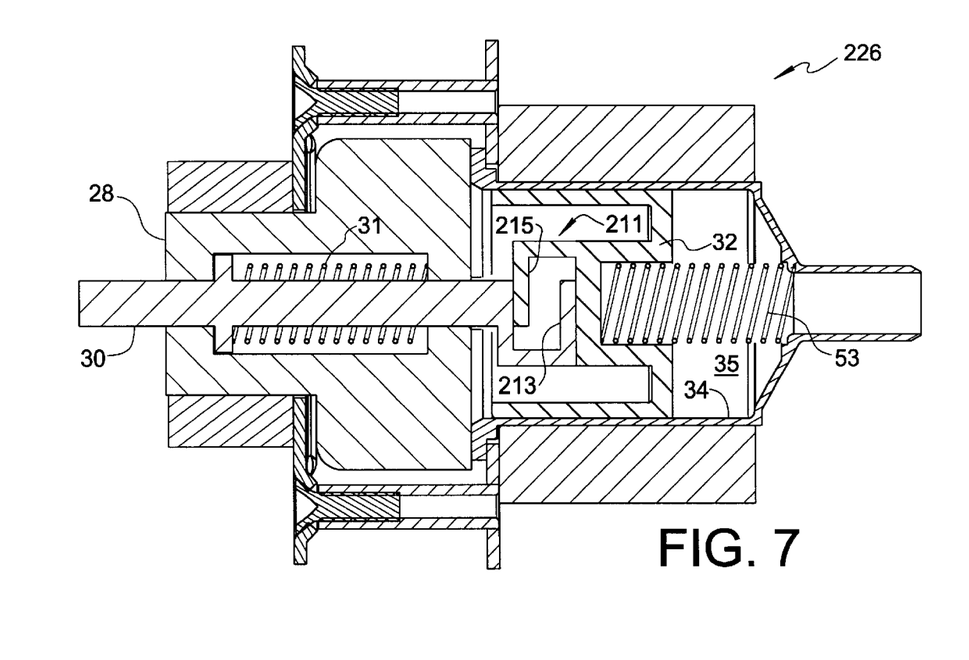
FIG. 7 is a cross-sectional view of a fluid pump formed in accordance with a further embodiment of the present invention.

FIG. 7 shows a tonometer fluid pump system 226 formed in accordance with a further embodiment of the present invention that is generally similar to the embodiment of FIG. 3. However, in the embodiment of FIG. 7, plunger 30 and piston 32 are linked by a push-pull coupling 211 permitting free radially directed movement of the piston independent of the plunger while providing movement of the piston in a return axial direction opposite the axial direction traveled during the compression stroke as the plunger returns to its initial reference position. Push-pull coupling 211 preferably includes a first U-shaped configuration 213 associated with a leading end of plunger 30 and a second U-shaped configuration 215 associated with a trailing portion of piston 32 or with a piston rod (not shown) to which piston 32 is fixed. The second U-shaped configuration 215 overlaps with and is inverted relative to first U-shaped configuration 213, thereby allowing piston 32 to be independent of plunger 30 with respect to a radial degree of freedom. Piston spring 53 is optional in this embodiment, but is preferably used to minimize impact noise in the fluid pump system.

Referring again to FIG. 3, it will be seen that plenum chamber 36 of fluid pump system 26 is provided by an axial hole through mounting member 27 and further defined by beam splitter 29 and objective lens 19. In addition, it will be seen that fluid discharge tube 24 comprises an inlet orifice 52 and an axially extending fluid passageway 54 connecting inlet orifice 52 with outlet orifice 42.

A preferred arrangement for optically detecting applanation of cornea C is shown schematically in FIG. 2. An infra-red emitter 60 is mounted on nosepiece 25 and obliquely aimed at corneal vertex V, and a photosensitive detector 62 is located on the opposite side of optical axis OA facing corneal vertex V along an oblique direction symmetrically opposite to that of applanation emitter 60. A collector lens (not shown) and a pinhole diaphragm (also not shown) are positioned in front of applanation detector 62, which is located in the focal plane of the collector lens. When the cornea C is in its normal convex shape, parallel incident rays from emitter 60 are reflected in a fanned-out fashion by the curved corneal surface, and a weak detection signal is generated at applanation detector 62. As a portion of the corneal surface approximates a flat surface at applanation, the incident parallel beam is reflected by the flat surface as a parallel beam in the direction of the collector lens, which focuses the beam through the pinhole diaphragm and onto the surface of applanation detector 62. As a result, applanation detector 62 registers a peak detection signal corresponding to applanation. Those familiar with non-contact tonometers will recognize that this arrangement for optically detecting applanation is already known from the prior art.

Tonometric measurement involves correlation of the pressure within plenum chamber 36 at applanation with IOP. Therefore, a pressure sensor 64, for example a pressure transducer or the like, is located within plenum chamber 36 for generating signal information indicative of the fluid pressure within the plenum chamber. As an alternative to directly pressure measuring plenum pressure using a pressure sensor, it is possible to indirectly measure plenum pressure by driving the fluid pump system 26' such that the pressure within plenum chamber 36 increases as a known function of time, and measuring the time required to achieve applanation as a correlate to IOP.

The analog signal information from pressure sensor 64 and applanation detector 62 is filtered and converted to digital form for processing by a central processing unit (CPU) 70. The plenum pressure at the time of applanation is then correlated to IOP by CPU 70. IOP measurement data are reported to the operator by liquid crystal display 20, and can be transmitted, preferably by wireless transmission, to a printing device and/or a remote computer.

What is claimed is:

1. In a non-contact tonometer of a type having a cylinder, a piston received by said cylinder for axially directed movement relative thereto, and a driven member for causing said piston to move in a first axial direction relative to said cylinder in a compression stroke to generate a fluid pulse, the improvement comprising:

said piston being independent of said driven member with respect to axial alignment of said piston with said cylinder.

2. The improvement according to claim 1, wherein said driven member includes an abutment end arranged to engage said piston such that said driven member pushes said piston during said compression stroke.

3. The improvement according to claim 2, wherein said abutment end of said driven member includes a protective cap.

4. The improvement according to claim 1, wherein said driven member includes an abutment end arranged to engage an intermediate member connected to said piston such that said driven member pushes said intermediate member and said piston during said compression stroke.

5. The improvement according to claim 4, wherein said abutment end of said driven member includes a protective cap.

6. The improvement according to claim 4, wherein said intermediate member is a piston rod.

7. The improvement according to claim 1, further comprising a spring acting between said cylinder and said piston for urging said piston in a second axial direction opposite said first axial direction in a return stroke of said piston.

8. A non-contact tonometer comprising:

a cylinder;

a piston received by said cylinder to define a fluid compression chamber, said piston being movable relative to said cylinder in a first axial direction to compress fluid within said compression chamber and in a second axial direction opposite said first axial direction;

an electromotive drive having a driven member arranged to cause said piston to move in said first axial direction, said piston being independent of said driven member with respect to a radial degree of freedom such that said piston is freely self-aligning relative to said cylinder;

a fluid discharge tube in flow communication with said compression chamber to direct a fluid pulse along a test axis to transfigure a cornea of a patient;

applanation detection means for monitoring said cornea and providing applanation signal information indicative of a state of applanation of said cornea caused by said fluid pulse;

means for determining a fluid pressure within said plenum chamber corresponding to said state of applanation of said cornea; and means for correlating said fluid pressure with an intraocular pressure of said eye.

9. The non-contact tonometer according to claim 8, wherein said electromotive drive is a linear solenoid.

10. The non-contact tonometer according to claim 8, wherein said electromotive drive is a rotary solenoid.

11. The non-contact tonometer according to claim 8, wherein said driven member includes an abutment end arranged to engage said piston such that said driven member pushes said piston during said compression stroke.

12. The non contact tonometer according to claim 11, wherein said abutment end of said driven member includes a protective cap.

13. The non-contact tonometer according to claim 8, wherein said driven member includes an abutment end arranged to engage an intermediate member connected to said piston such that said driven member pushes said intermediate member and said piston during said compression stroke.

14. The non-contact tonometer according to claim 13, wherein said abutment end of said driven member includes a protective cap.

15. The non-contact tonometer according to claim 13, wherein said intermediate member is a piston rod.

16. The non-contact tonometer according to claim 8, further comprising a spring acting between said cylinder and said piston for urging said piston in said second axial direction to return said piston to a stroke start position thereof.

17. The non-contact tonometer according to claim 8, wherein said electromotive drive forces said driven member away from an initial reference position to cause said piston to move in said first axial direction, and said electromotive drive includes means for returning said driven member to said initial reference position.

18. The non-contact tonometer according to claim 17, wherein said driven member and said piston are linked by a push-pull coupling permitting free radially directed movement of said piston independent of said driven member while providing movement of said piston in said second axial direction as said driven member returns to said initial reference position.

19. The non-contact tonometer according to claim 18, wherein said push-pull coupling includes a first U-shaped configuration associated with said driven member and a second U-shaped configuration associated with said piston, wherein said second U-shaped configuration overlaps with and is inverted relative to said first U-shaped configuration.

20. The non-contact tonometer according to claim 16, wherein said electromotive drive forces said driven member away from an initial reference position to cause said piston to move in said first axial direction, and said electromotive drive includes means for returning said driven member to said initial reference position.

21. The non-contact tonometer according to claim 20, wherein said means for returning said driven member to said initial reference position is a spring.

22. The non-contact tonometer according to claim 21, wherein said spring for urging said piston in said second axial direction causes said piston to move more slowly to said stroke start position than said spring for returning said driven member causes said driven member to return to said initial reference position.

23. A non-contact tonometer comprising:

a cylinder;

a piston received by said cylinder to define a fluid compression chamber, said piston being movable relative to said cylinder in a first axial direction to compress fluid within said compression chamber and in a second axial direction opposite said first axial direction;

a linear solenoid having a driven plunger arranged for transmitting force to said piston by contact therewith to move said piston in said first axial direction, said piston being adjacent but unattached to said driven plunger;

a fluid discharge tube in flow communication with said compression chamber to direct a fluid pulse along a test axis to transfigure a cornea of a patient;

a light source spaced from said fluid discharge tube for emitting a beam of light toward said eye for reflection by a cornea of said eye;

a light sensitive detector arranged to receive corneally reflected light and provide applanation signal information indicative of corneal transfiguration caused by a fluid pulse generated by said fluid pump and directed at said eye through said fluid discharge tube;

a pressure transducer arranged to detect fluid pressure within said plenum chamber and provide pressure signal information indicative of said plenum pressure; and signal processing means for receiving said applanation signal information and said pressure signal information and calculating an intraocular pressure value therefrom.

24. The non-contact tonometer according to claim 23, wherein said driven plunger includes an abutment end arranged to engage said piston such that said driven member pushes said piston during said compression stroke.

25. The non-contact tonometer according to claim 24, wherein said abutment end of said driven plunger includes a protective cap.

26. The non-contact tonometer according to claim 23, further comprising a spring acting between said cylinder and said piston for urging said piston in a second axial direction opposite said first axial direction to return said piston to a stroke start position thereof.

27. The non-contact tonometer according to claim 26, wherein said spring bears against a front wall of said cylinder and a leading surface of said piston.

28. The non-contact tonometer according to claim 27, wherein said spring is a coil spring that is coaxial with said piston and said cylinder.

29. The non-contact tonometer according to claim 28, wherein said leading surface of said piston includes a recess for receiving a portion of said spring.

\* \* \* \* \*